(12) United States Patent
Pedack

(10) Patent No.: US 6,280,033 B1
(45) Date of Patent: Aug. 28, 2001

(54) INDIRECT OPHTHALMOSCOPE

(75) Inventor: Henry Pedack, Bellingham, WA (US)

(73) Assignee: Keeler Limited (GB)

( * ) Notice: Subject to any disclaimer, the term of this patent is extended or adjusted under 35 U.S.C. 154(b) by 0 days.

(21) Appl. No.: 09/521,643

(22) Filed: Mar. 8, 2000

(51) Int. Cl.⁷ ..................................................... A61B 3/10
(52) U.S. Cl. ............................................................ 351/216
(58) Field of Search .................................. 351/205, 221, 351/218, 245, 216

(56) References Cited

U.S. PATENT DOCUMENTS

| | | | |
|---|---|---|---|
| 4,461,551 | 7/1984 | Blaha | 351/214 |
| 4,856,872 | 8/1989 | Spitznas et al. | 350/255 |
| 5,282,085 | 1/1994 | Volkert et al. | 359/377 |
| 5,526,074 | 6/1996 | Volk | 351/219 |
| 5,629,747 | * 5/1997 | Miyake | 351/218 |
| 5,793,524 | 8/1998 | Luloh | 359/381 |
| 5,838,421 | * 11/1998 | Pedack | 351/218 |

FOREIGN PATENT DOCUMENTS 0 065 750  12/1982  (DE) .

* cited by examiner

Primary Examiner—George Manuel
(74) Attorney, Agent, or Firm—Lee, Mann, Smith, McWilliams, Sweeney & Ohlson

(57) ABSTRACT

An indirect ophthalmoscope is used in the observation of the eye, and comprises viewing optics through which, in use, at least part of said eye is viewed. Light from the eye travels to and through the viewing optics along a viewing path, and the ophthalmoscope includes a lens (36) which is movable between an operative position (in which it is situated in the viewing path) and an inoperative position (in which it is situated clear of the viewing path). The lens 36 can be used to enable the observer to see a magnified image of the eye under examination.

14 Claims, 3 Drawing Sheets

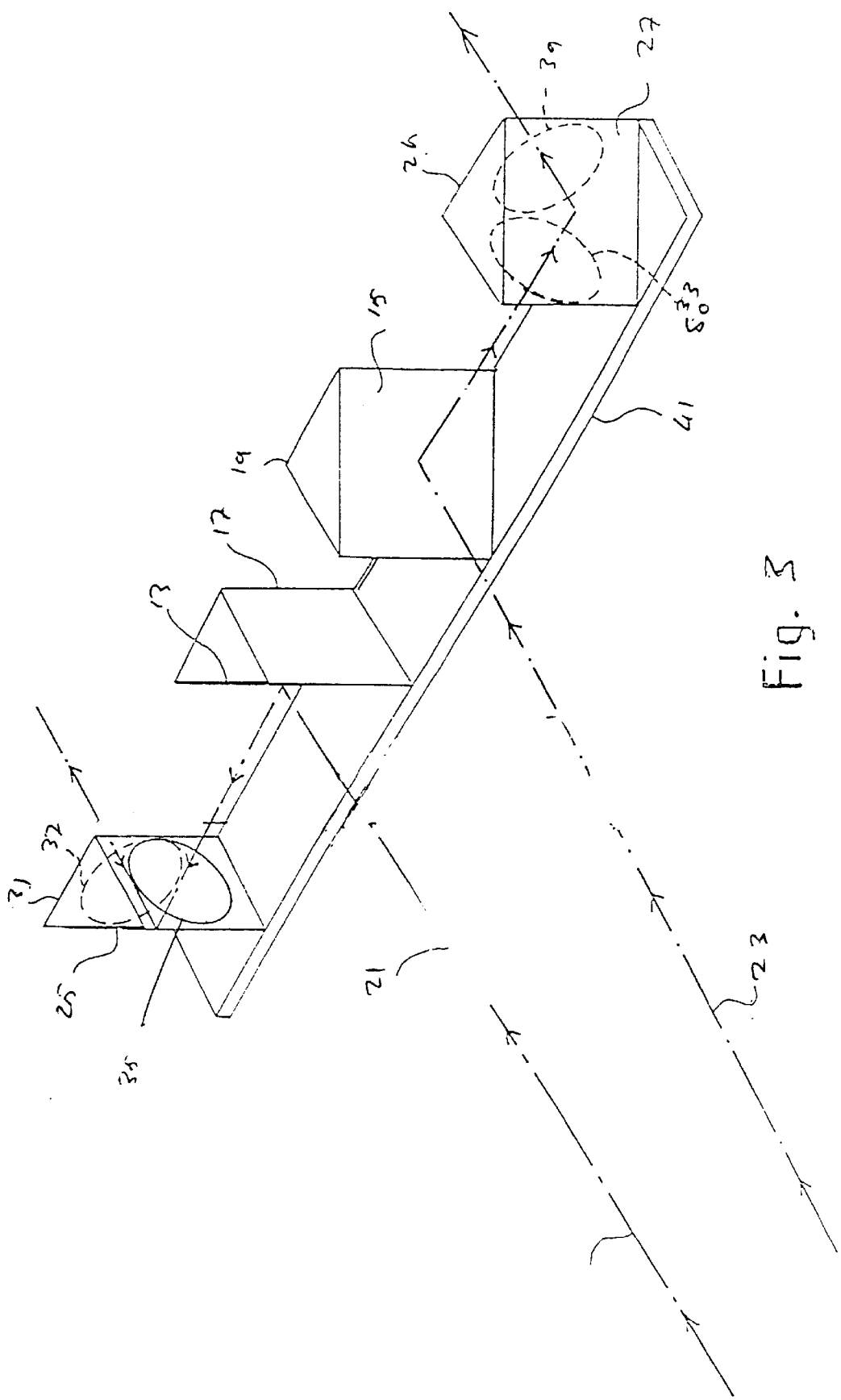

INDIRECT OPHTHALMOSCOPE

FIELD OF THE INVENTION

This invention relates to indirect ophthalmoscopes.

BACKGROUND TO THE INVENTION

In diagnostic and operative retinal practice, binocular indirect ophthalmoscopy is widely accepted as a fundamental method of examination of the retina of an eye. Typically, an indirect ophthalmoscope includes illuminating optics for illuminating the retina and viewing optics through which the image of the retina is viewed, and is mounted on a headband which enables it to be attached to the head of a user. The ophthalmoscope is used in conjunction with a hand held condensing ophthalmoscopy lens which the user positions between the viewing optics and the eye under examination so as to form an image of the retina between the lens and the viewing optics.

Compared with direct ophthalmoscopes, indirect ophthalmoscopes provide a relatively wide field of view and bright illumination of the retina under examination. However, this view is of a relatively low magnification.

It has been proposed to improve the magnification of an indirect ophthalmoscope by re-configuring the viewing optics so that the latter act as telescopes. However, this increases the complexity of the viewing optics and can adversely affect the size and weight of the ophthalmoscope. In addition, such an ophthalmoscope is no longer suitable for providing low magnification views.

SUMMARY OF THE INVENTION

According to the invention, there is provided an indirect ophthalmoscope for use in the observation of an eye, the ophthalmoscope comprising viewing optics through which, in use, at least part of said eye is viewed, light from the eye travelling to and through the viewing optics along a viewing path, wherein the ophthalmoscope includes a lens so mounted thereon as to be movable between an operative position, in which it is situated in said viewing path so as to refract light from the eye under examination, and an inoperative position, in which the lens is situated clear of the viewing path.

Thus the movable lens can enable the user to alter the size of image viewed through the viewing optics. If the viewing optics incorporate telescopic systems, the lens may, for example, be a diverging lens which reduces the magnification of the final image.

Preferably, however, the lens is a converging lens which, when in its operative position, acts as a magnifying lens for the image viewed through the ophthalmoscope.

When this lens is in its operative position, and the image formed directly by the hand held ophthalmoscopy lens is closer to the movable lens than the focal length of the latter, the movable lens acts as a magnifying glass which creates an enlarged virtual image of the retina further away from the viewing optics than the image formed by the ophthalmoscopy lens. This enables the user to see a focused image of the retina from a closer position than would be possible without the movable lens.

Preferably, the movable lens is a meniscus lens, preferably of a power of approximately +3 dioptre.

The lens may to advantage be mounted in front of the viewing optics so that, when in its operative position, it is interposed between the viewing optics and the eye under examination.

Preferably, the lens is pivotally mounted on the front of the ophthalmoscope so that movement between the operative and inoperative positions is achieved by pivoting the lens.

In this case, the lens is conveniently connected to a manually operated control member, preferably a rotary member, movable to cause said pivotal movement.

Preferably, the lens is mounted on the ophthalmoscope through a mounting bracket.

Preferably, the ophthalmoscope is a binocular device, the viewing optics being one of a pair of such viewing means for enabling an eye under examination to be viewed along corresponding left and right eye viewing paths, wherein the lens, when in its operative position, is situated in both viewing paths.

Preferably, the ophthalmoscope is attached to mounting means (for example a headband or headgear) for mounting it on the head of a user.

Another advantage of the movable lens is that it can be retrofitted to existing ophthalmoscopes without having to make any adjustment or modification to their viewing optics. In addition, since the ophthalmoscope can be positioned closer to the eye under examination, the user will obtain a better three-dimensional image (if the ophthalmoscope is a binocular device) because of the greater angle of convergence of the left and right eye viewing paths of the viewing optics on the retina under examination.

BRIEF DESCRIPTION OF THE DRAWINGS

The invention will now be described, by way of example only, with reference to the accompanying drawings, in which;

FIG. 3 is a schematic view of part of the viewing optics of the ophthalmoscope.

DETAILED DESCRIPTION

Figure 1:
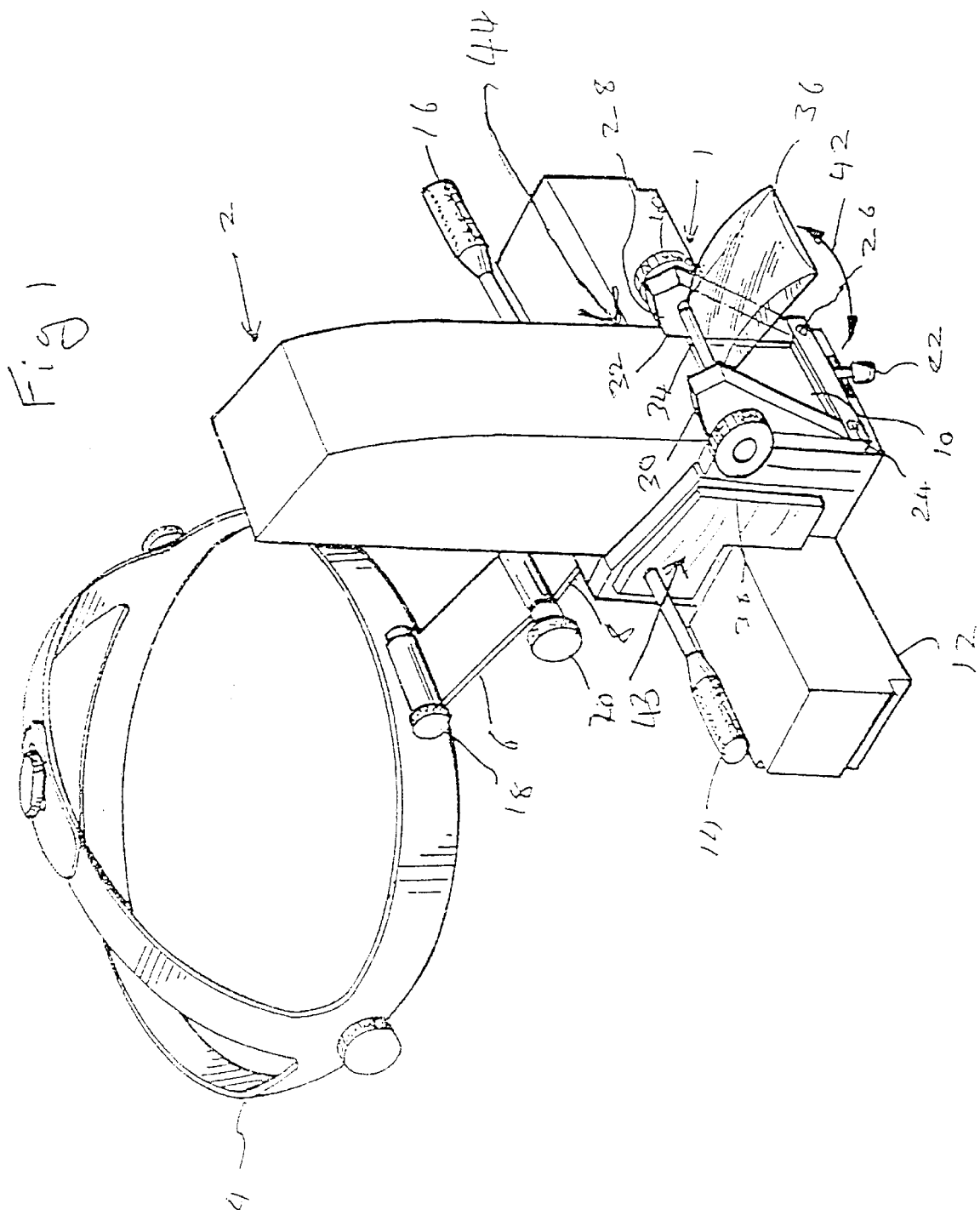
FIG. 1 is a perspective view of an embodiment of a binocular indirect ophthalmoscope in accordance with the invention.

The drawing shows one of the present applicant's ophthalmoscopes, identified by the Trade Mark KEELER VANTAGE, which has been modified by the addition of a further lens assembly, generally referenced 1.

The ophthalmoscope comprises a housing 2 which is in the general shape of an inverted T. The housing contains illumination and left and right eye viewing optics, and is attached to a headband 4 which enables the ophthalmoscope to be mounted on the head of a user (for example, an ophthalmologist). The housing 2 is attached to the front of the headband 4 via two arms 6 and 8, which are pivoted together and to the headband and housing 2 respectively, and which enable the distance between the housing 2 and the face of the user to be adjusted.

The connections between the two arms 6 and 8 and the headband 4 and the arm 6 and the arm 8 and the housing 2 are provided with nuts, for example 18 and 20, which can be tightened to fix the housing 2 at a desired position relative to the headband 4.

Figure 2:
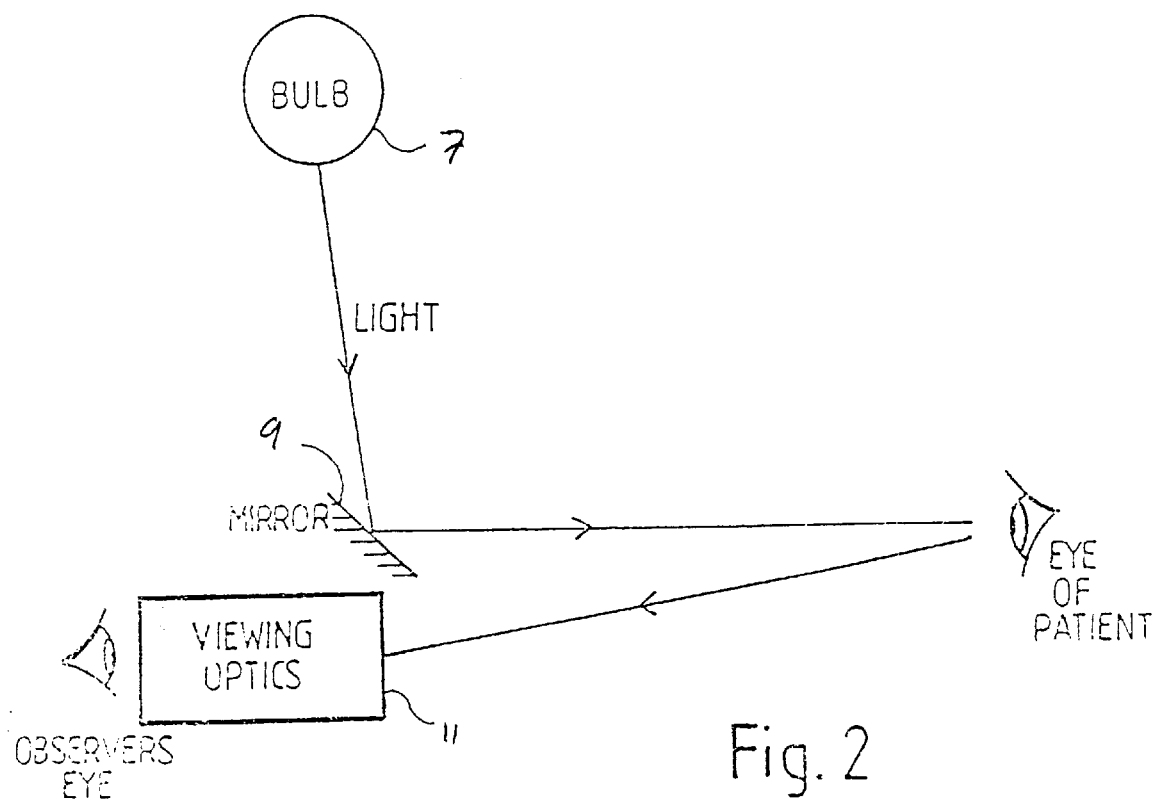
FIG. 2 is a schematic side view of the viewing optics and illumination optics of the ophthalmoscope.

The vertical stem of the housing 2 contains the illumination optics for illuminating a retina to be examined. The illumination optics comprise a light bulb 7 (FIG. 2) at the top of the housing 2, and an angled mirror 9 positioned underneath the light source so as to reflect light from the latter out through a window 10 in the front face of the housing 2. The mirror is positioned immediately above the viewing optics 11 (situated in the cross-piece 12 of the housing), and is mounted in the housing 2 via an adjustment mechanism which enables the angulation of the mirror 9 to be adjusted by rotation of either of two control knobs 14 and 16 projecting horizontally from the sides of the stem of the housing 2. Vertical separation between the mirror 9 and the viewing optics can be varied by vertically moving control knobs 14 and 16 or by raising or lowering plates 43 and 44 on the opposite side of the housing stem from the plate 42. This adjustment of the height of the mirror 9, in combination with an adjusted angulation of the mirror 9, enables the vertical angle between the path along which light illuminates the retina under examination and the viewing path to be adjusted. When the ophthalmoscope is used at a relatively short distance from the eye under examination, the mirror 9 can be moved further towards the viewing optics to decrease the angle between the illumination path and the viewing path so as to allow both paths to pass through the pupil of the eye under examination. When the ophthalmoscope is used at greater distances, however, the mirror 9 can be moved further from the viewing optics so that corneal reflexes can be reduced.

With reference to FIG. 3, the viewing optics 11 comprise a pair of laterally spaced mirrors 13 and 15 which are mounted on triangular mirror blocks 17 and 19. The mirrors 13 and 15 are angled so as to direct light travelling into the window 10 (along the viewing paths 21 and 23) horizontally outwards to the reflective surfaces of the mirrors 25 and 27 mounted on triangular mirror blocks 29 and 31 which have apertures (33 and 35) to allow the light to reach the mirrors 25 and 27. Further apertures (37 and 39) in the blocks 29 and 31 enable the light reflected by the mirrors 25 and 27 to travel to eyepieces (not shown) situated behind the platform 41 on which the mirror blocks are mounted. The spacing between the mirrors can be adjusted by means of a lever 22 in order to adjust the stereopsis of the ophthalmoscope.

Since the illuminating and viewing optics within the housing 2 are part of a proprietary ophthalmoscope (i.e. the KEELER VANTAGE), they have not been shown in the drawing.

The front of the housing 2 is provided with screw holes at 24 and 26 via which a generally U-shaped mounting bracket 28 is screwed onto the housing 2.

The bracket 28 has a pair of opposed side arms 30 and 32 through which a horizontal shaft 34 extends.

The shaft 34 carries a radial meniscus converging lens 36, and is terminated at each end by a respective knob 38 and 40 which can be turned to rotate the shaft 34, and hence the lens 36, in either direction indicated by the double-headed arrow 42.

The frictional interaction between the arms 30 and 32 and the portions of the shaft 34 passing therethrough is sufficient to hold the shaft 34 and hence the lens 36 in a selected angular position.

The power of the lens 36 is +3 dioptre. Since the shaft 34 extends over the top of the front of the window 10, the lens 36 can be moved in the directions indicated by the arrow 42 between a lowered position, in which the lens 36 covers the window 10 and a raised position in which the lens 36 presents no obstruction to the window 10. When the lens 36 is raised into this position, it is in its inoperative position, and as a result the ophthalmoscope functions in the same way as a standard KEELER VANTAGE indirect ophthal-moscope. Consequently, the ophthalmoscope has the same magnification power and minimum working distance (i.e. between the real image of the retina formed by the hand held lens (not shown) and the mirrors of the viewing optics) below which the user would not be able to focus on the image of the retina.

If the user wishes to obtain a "closer" view of the retina, he or she can simply use the hand not holding the ophthalmoscopy lens to rotate the lens 36 into its operative position (in which it covers the window 10). The user positions the ophthalmoscope close to the eye under examination, so that the image formed by the ophthalmoscopy lens will be closer to the lens 36 than the focal length of the latter. As a result, the lens 36 will form an image of the retina at a position at or greater than said minimum working distance.

It will be appreciated that, when in its operative position, the lens 36 magnifies the images seen by both the left and right eye of the user, since it encompasses both the associated viewing paths 21 and 23 from the eye under examination.

The image formed by the lens 36 will be linearly magnified compared with that formed by the ophthalmoscopy lens, but will be further away from the viewing optics than the latter. Thus, the lens 36 has the effect of magnifying the image seen by the user, since the user can focus on the retina from a closer distance than-would otherwise be possible.

What is claimed is:

1. An indirect ophthalmoscope for use in the observation of an eye, the ophthalmoscope comprising viewing optics through which, in use, at least part of said eye is viewed, light from the eye travelling to and through the viewing optics along a viewing path, wherein the ophthalmoscope includes a lens so mounted thereon as to be movable between an operative position, in which it is situated in said viewing path so as to refract light from the eye under examination, and an inoperative position, in which the lens is situated clear of the viewing path.

2. An indirect ophthalmoscope according to claim 1, in which the lens is of a focal length which is such as to enable the user to alter the size of image viewed through the viewing optics.

3. An indirect ophthalmoscope according to claim 2, in which the lens is a converging lens which, when in its operative position, act s as a magnifying lens for the image viewed through the ophthalmoscope.

4. An ophthalmoscope according to claim 3, in which the lens is a meniscus lens.

5. An ophthalmoscope according to claim 3, in which the lens has a power of approximately +3 dioptre.

6. An ophthalmoscope according to claim 1, in which the lens is mounted in front of the viewing optics so that, when in its operative position, it is interposed between the viewing optics and the eye under examination.

7. An ophthalmoscope according to claim 6, in which the lens is pivotally mounted on the front of the ophthalmoscope so that movement between the operative and inoperative positions is achieved by pivoting the lens.

8. An ophthalmoscope according to claim 7, in which the lens is connected to a manually operated control member, movable to cause said pivotal movement.

9. An ophthalmoscope according to claim 8, in which the control member is a rotary member.

10. An ophthalmoscope according to claim 1, in which the lens is mounted on the ophthalmoscope through a mounting bracket.

11. An ophthalmoscope according to claim 1, in which the ophthalmoscope is a binocular device, the viewing optics being one of a pair of such viewing means for enabling an eye under examination to be viewed along corresponding left and right eye viewing paths, wherein the lens, when in its operative position, is situated in both viewing paths.

12. An ophthalmoscope according to claim 1, in which the ophthalmoscope is attached to mounting means for mounting it on the head of a user.

13. A magnifying device for a binocular indirect ophthalmoscope, the device comprising a magnifying lens movably mounted on a mounting bracket adapted to be attached to the front of an ophthalmoscope, wherein, with the device attached to an ophthalmoscope, the lens is movable between an operative position in which it magnifies both left and right eye images seen through the ophthalmoscope and an inoperative position in which it does not affect the size of said images.

14. An indirect ophthalmoscope for use in the observation of an eye, the ophthalmoscope comprising viewing optics for enabling the user to view at least part of said eye, light traveling from said eye to the viewing optics and the user along a viewing path, wherein the ophthalmoscope also includes a movable lens carried thereby and movable between an operative position in which it is situated in the viewing path so as to refract light from the eye under examination, and an inoperative position in which it is situated clear of the viewing path, wherein the viewing optics are operable to enable the user to view at least part of the eye under examination when the movable lens is in its operative position and when no lens is in said position.

* * * * *